US008485357B2

United States Patent
Song et al.

(10) Patent No.: US 8,485,357 B2
(45) Date of Patent: Jul. 16, 2013

(54) TRAY FOR POSITIONING ELONGATED OBJECTS, IN PARTICULAR SYRINGE BODIES OR SYRINGES

(75) Inventors: Xu Song, Short Hills, NJ (US); Behzad Mottahed, Upper Montclair, NJ (US); Ruane Jeter, Los Angeles, CA (US); Samuel Gagniuex, Echirolles (FR); Antoine Boulet, Voiron (FR); Franck Carrel, Le Point de Claix (FR); Nicolas Eon, Grenoble (FR)

(73) Assignee: Becton Dickinson France, Le Pont de Claix (FR)

( * ) Notice: Subject to any disclaimer, the term of this patent is extended or adjusted under 35 U.S.C. 154(b) by 0 days.

(21) Appl. No.: 13/382,237

(22) PCT Filed: Jul. 15, 2009

(86) PCT No.: PCT/IB2009/006701
§ 371 (c)(1),
(2), (4) Date: Jan. 4, 2012

(87) PCT Pub. No.: WO2011/007194
PCT Pub. Date: Jan. 20, 2011

(65) Prior Publication Data
US 2012/0103861 A1  May 3, 2012

(51) Int. Cl.
*B65D 83/10* (2006.01)
*B65D 85/20* (2006.01)
*A47F 7/00* (2006.01)

(52) U.S. Cl.
USPC ............. 206/366; 206/443; 211/60.1; 211/74

(58) Field of Classification Search
USPC . 206/366, 370, 443, 526, 563, 564; 211/60.1, 211/74
See application file for complete search history.

(56) References Cited

U.S. PATENT DOCUMENTS

| 4,349,338 | A | 9/1982 | Heppler |
| 5,667,495 | A | 9/1997 | Bitdinger et al. |
| 5,850,917 | A | 12/1998 | Denton et al. |
| 8,100,263 | B2* | 1/2012 | Vanderbush et al. ......... 206/366 |
| 2006/0016156 | A1 | 1/2006 | Bush et al. |
| 2008/0183140 | A1* | 7/2008 | Paproski et al. ............. 604/110 |
| 2009/0100802 | A1 | 4/2009 | Bush et al. |

FOREIGN PATENT DOCUMENTS

WO   2008067467 A2   6/2008

* cited by examiner

*Primary Examiner* — Bryon Gehman
(74) *Attorney, Agent, or Firm* — The Webb Law Firm

(57) ABSTRACT

A tray for positioning elongated objects each having a body and a flange. The tray includes a plate with openings and bearing surfaces. At least one first bearing surface is near a first opening and located at a first distance from the plate of the tray, and at least one second bearing surface is near a second opening adjacent the first opening and located at a second distance from the plate of the tray. The second distance is different from the first distance. The first and second openings are located at a distance with respect to one another such that the flange of a first elongated object engaged in one of these openings is able to partially overlap the flange of a second elongated object engaged in the other of these openings without contact between the flange of the first elongated object and the flange of the second elongated object.

12 Claims, 8 Drawing Sheets

TRAY FOR POSITIONING ELONGATED OBJECTS, IN PARTICULAR SYRINGE BODIES OR SYRINGES

The present invention relates to a tray for positioning elongated objects, in particular syringe bodies or syringes, these elongated objects comprising bodies, notably cylindrical, and flanges. In the case of a syringe body, the flange is located at one end of the cylindrical body, or near this end. The flange can be integral with the syringe body or can be formed by a separate part mounted on the proximal end of this body.

It is frequent that syringe bodies or syringes are to be transported from one site to another site, either when they are manufactured on a site and are filled on another site, or when they are manufactured and filled on the same site and are to be used on another site.

For this transport, it is current to group the syringe bodies or syringes on a tray having openings and tubular walls or chimneys coaxially surrounding these openings, the openings receiving the syringe bodies and the flanges bearing against said tubular walls or chimneys. The tray with the syringe bodies or syringes thereon is placed in a packaging box, which is sealed and sterilized. At destination, the box is opened and the tray is extracted therefrom, the tray being subsequently used for handling and/or filling of the syringe bodies or syringes by automated means.

A known tray for grouping syringe bodies or syringes includes a plate and a plurality of chimneys projecting from at least a face of this plate, these chimneys being dimensioned to receive the syringe bodies or syringes through them until the flanges of the syringe bodies or syringes bear against the upper free edges of these chimneys.

With this tray, however, the number of syringe bodies or syringes that can be installed on a same tray is limited. This limitation has a direct consequence on the number of packaging boxes having to be used to transport a given number of syringe bodies or syringes and thus on the cost of the packaging and of the transport of these syringe bodies or syringes. For the user, it is necessary to open and handle a significant number of packaging boxes to process a given number of syringe bodies or syringes.

The object of the present invention is to limit this drawback.

The tray concerned includes, in a known way, a plate with spaced apart openings intended to receive the bodies of the elongated objects and bearing surfaces near said openings to receive the flanges of these elongated objects when said bodies are engaged in said openings.

According to the invention,
the tray includes at least one first bearing surface near a first opening, located at a first distance from the plate of the tray, and at least one second bearing surface near a second opening adjacent said first opening, located at a second distance from the plate of the tray, said second distance being different from said first distance;
said difference between said first and second distance is such that said flange of the object engaged in one of these openings is able to rotate in this opening without contact with the flange of the object engaged in the other of these openings.

Said first and second bearing surfaces of the tray according to the invention thus make it possible to position the flanges of the elongated objects at different heights from an opening to an adjacent opening, so that the flanges of the objects engaged in these two openings can rotate without contact one with the other.

It is thus possible to arrange the openings in positions notably closer than the openings of a tray according to the prior art, and thus to significantly increase the density of these objects on this tray, while allowing the external dimensions of the tray to remain identical to those of the existing trays. This conservation of these external dimensions is indeed necessary not to induce too important modifications of the automated treatment units of the elongated objects, in particular of the units for handling and/or filling syringe bodies.

This increase in the density of the number of elongated objects makes it possible to reduce the number of packagings that are necessary for the conditioning and the transport of a given number of these objects, and thus to reduce the costs of conditioning and transporting these objects. The subsequent operations of opening and handling the boxes containing these objects are also reduced accordingly.

Preferably,
said first and second openings are located at a distance one with respect to the other such that the flange of the object engaged in one of these openings is able to partially overlap the flange of the object engaged in the other of these openings, and
said difference between said first and second distance is such that said flange of the object engaged in one of these openings is able to partially overlap the flange of the object engaged in the other of these openings without contact with this flange.

The density of elongated objects can thus be further increased accordingly.

Said first bearing surface can coincide with the surface of the plate of the tray, being thus formed by this surface. This first bearing surface can also not coincide with the surface of the plate of the tray, being thus formed by a projection which the plate of the tray includes.

This projection can have any suitable form making it possible to constitute said first bearing surface, in particular it can be in the form of one or several walls or studs. Preferably, this projection is in the form of a substantially tubular wall or chimney coaxial to said first opening.

According to a possible embodiment, the openings of the tray are arranged according to series of openings, each opening of a first series having said first bearing surface and each opening of a second series of openings, adjacent said first series, having said a second bearing surface.

According to a preferred embodiment, the plate includes alternated first and second series of openings, the bearing surfaces of the first series of openings being formed by the surface of the plate of the tray and the bearing surfaces of the second series of openings being formed by the free edges of tubular walls, each one of these tubular walls being coaxial to one opening of each one of these second series.

According to another possible embodiment, the plate includes first, second, . . . , n−1, n series of openings and first, second, . . . , n−1, n series of bearing surfaces respectively associated with each one of these series of openings, the first bearing surfaces of the first series of openings being located at a first distance from the plate of the tray, the second bearing surfaces of the second series of openings being located at a second distance from the plate of the tray, higher than said first distance, and the n bearing surfaces of the n series of openings being located at a n distance from the plate of the tray, higher than the distance n−1 of the n−1 series of openings.

In other words, the distances of the bearing surfaces to the plate of the tray constantly increase from the first series of openings to the n series of openings.

According to another aspect, the invention relates to a packaging unit for packaging elongated objects, in particular syringes bodies or syringes, including a first tray for positioning elongated objects and a support structure for supporting this first tray, including a first reception area for receiving said first tray, this first tray including openings for the reception of the elongated objects.

According to the invention, the packaging unit includes a second tray with openings for the reception of elongated objects and said support structure includes a second reception area, intended to receive this second tray, this second reception area being arranged so as to position this second tray on said support structure, opposite the first tray and so that the openings of said second tray are offset with respect to the openings of said first tray, this offset being such that each opening of the first tray is located apart from the perimeter of each opening of the second tray, this second tray being positioned with respect to the first tray such that elongated objects engaged in the openings of the first tray can imbricate with elongated objects engaged in the openings of the second tray, and vice versa.

The same support structure can thus contain a doubled or substantially doubled number of elongated objects.

Said support structure can be constituted by a packaging box, said first and second reception areas being formed by respective bearing surfaces arranged on the walls of this box.

According to a possibility, said first tray and said second tray are identical one to the other, and said first reception area and second reception area are formed so as to position the edges of the two plates in an offset way one with respect to the other, thus allowing the above-mentioned offset of the openings of the trays.

According to another possibility, said first tray includes openings offset with respect to the openings of said second tray, and said first reception area and second reception area are formed so as to position the edges of the two trays opposite one the other.

The invention will be well understood, and other characteristics and advantages thereof will appear, in reference to the appended diagrammatic drawing, illustrating, as a non-limiting example, preferred embodiments of the tray and of the packaging unit it concerns.

Figure 1:
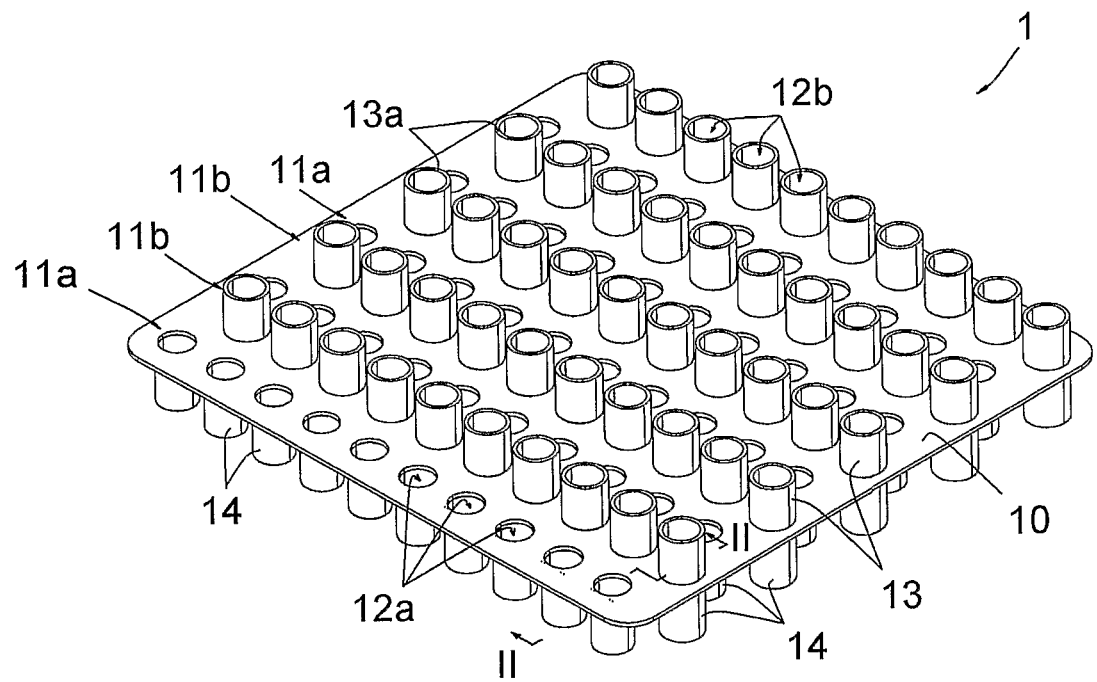
FIG. 1 is a perspective view of the tray according to a first embodiment.

The FIGS. 1-6 show a tray 1 for positioning syringe bodies 2 comprising cylindrical bodies 2a and flanges 2b located at one end of the cylindrical bodies 2a. The syringe bodies 2 are usually made of glass and the flanges 2b are integral with the cylindrical bodies 2a. This tray 1 is used to group the syringe bodies 2 for the transport of these syringe bodies 2 from one site to another site when the syringe bodies 2 are manufactured on a site and are filled on another site.

The tray 1 can also be used to group filled syringes 3 as shown on FIGS. 9-12, when, less frequently, the syringes are manufactured and filled on the same site and are to be used on another site. As can be seen particularly on FIG. 10, flanges 4, or "backstops", formed by separated parts, are mounted on the flanges 2b of the syringe bodies 2 so as to make resting portions for the fingers of a user at the moment of an injection and to make stops preventing the withdrawal of the syringe plungers 2c. The document U.S. Pat. No. 5,667,495 discloses backstops as shown on the FIGS. 9-12.

For the transport, the tray 1 with the filled syringe 3 thereon is placed in a packaging box 5 (shown on FIGS. 7 and 11), which is sealed by a membrane and sterilized. At destination, the box 5 is opened and the tray 1 is extracted therefrom, this tray 1 being subsequently used for handling the syringe bodies 2 or the syringes 3 by automated means.

Figure 2:
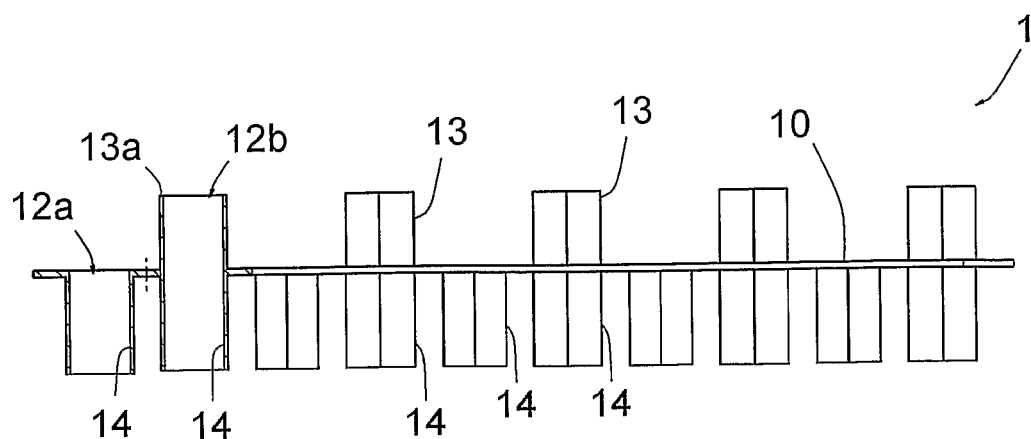
FIG. 2 is a side view of the tray of FIG. 1, partially in cross section along the line II-II of FIG. 1.
Figure 3:
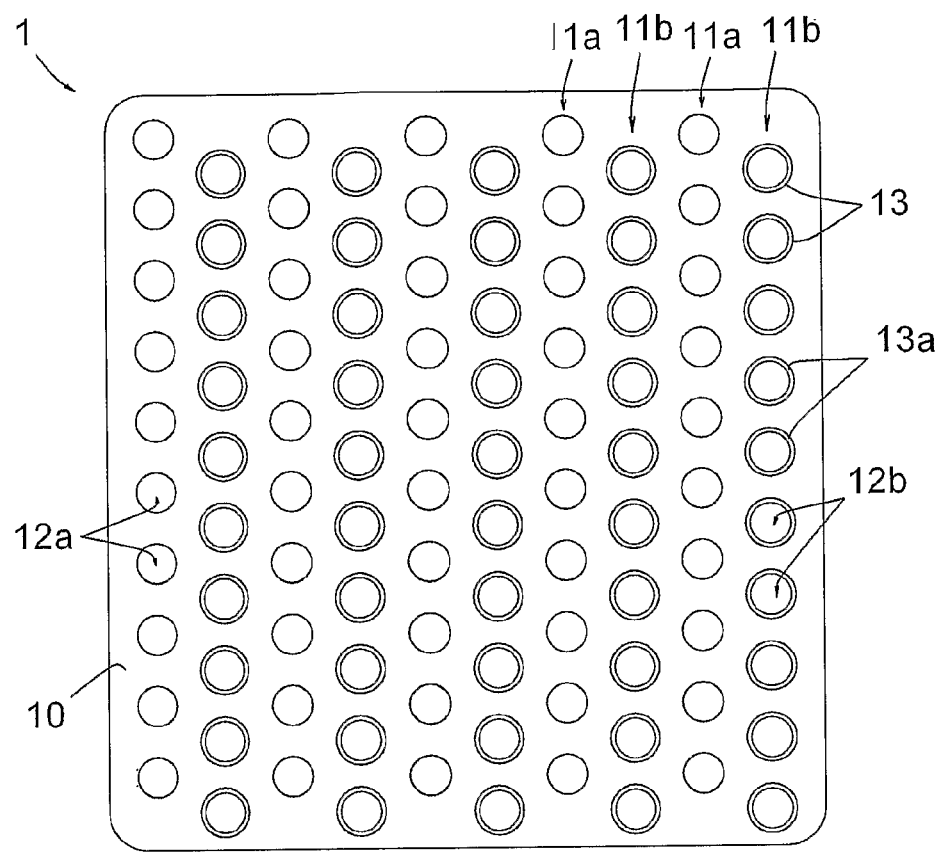
FIG. 3 is a top plan view of the tray of FIG. 1.

In reference to FIGS. 1-3, the tray 1 includes a plate 10 with alternated rows 11a, 11b of spaced apart openings 12a, 12b intended to receive the syringe bodies 2 or the syringes 3. On the upper face of the plate 10, as can be seen on the FIGS. 1-3, the openings 12a of the rows 11a opens directly in the upper face of plate 10 and the openings 12b of the lines 11b are formed by the free edges 13a of tubular walls or chimneys 13 integral with the plate 10, these chimneys 13 also forming bottom openings through the plate 10. The upper face of the plate 10 thus forms first bearing surfaces around the openings 12a, that coincide with this upper face, and the free edges 13a of the chimneys 13 form second bearing surfaces around the openings 12b located at a distance from this upper face.

The tray 1 includes, on the lower face of the plate 10, tubular chimneys 14 integral therewith and coaxial with the respective openings 12a and 12b. As can be seen on FIG. 2, the chimneys 14 form smooth conduits with respectively the openings 12a and the chimneys 13.

Figure 4:
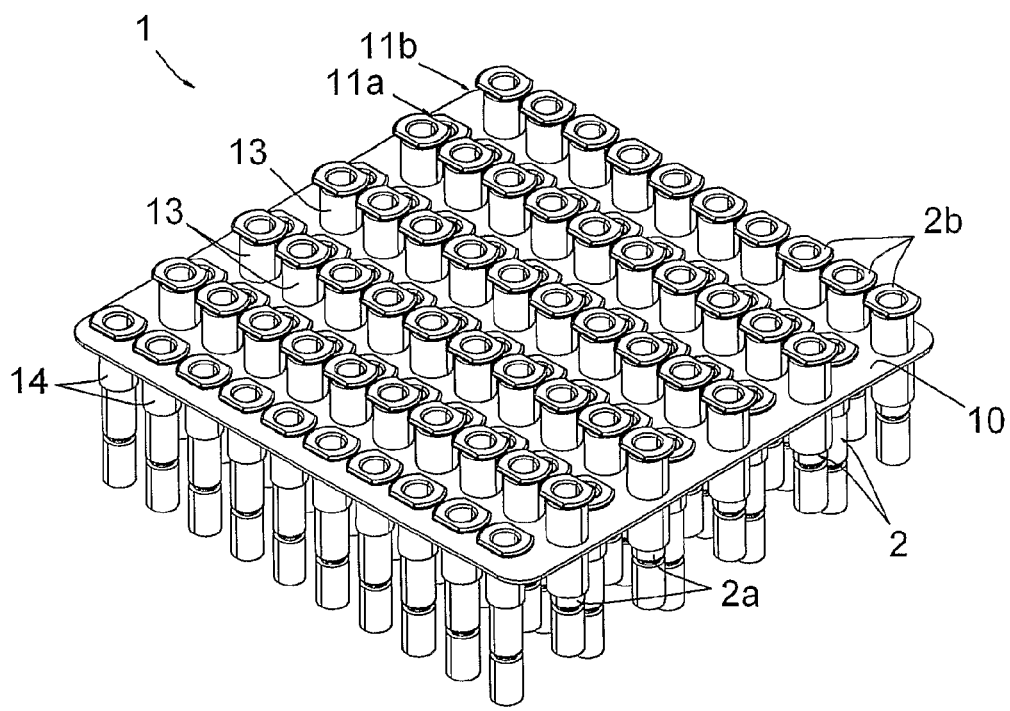
FIG. 4 is a perspective view of the tray of FIG. 1 after putting in place syringe bodies thereon.
Figure 9:
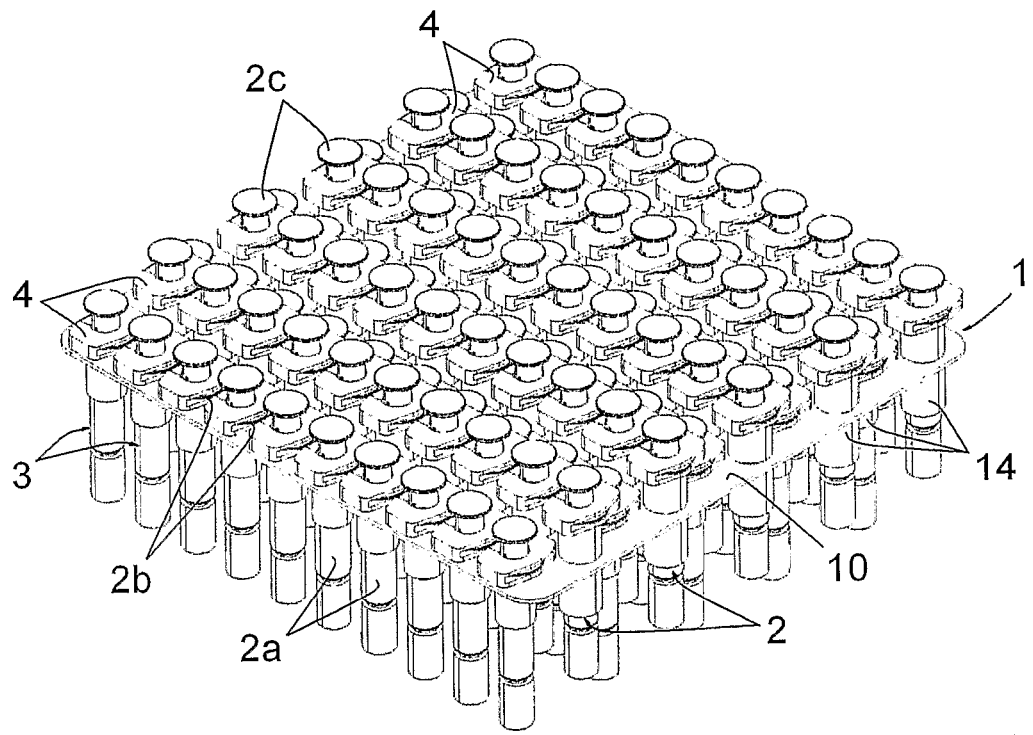
FIG. 9 is a perspective view of the tray of FIG. 1 after putting in place syringes thereon.
Figure 10:
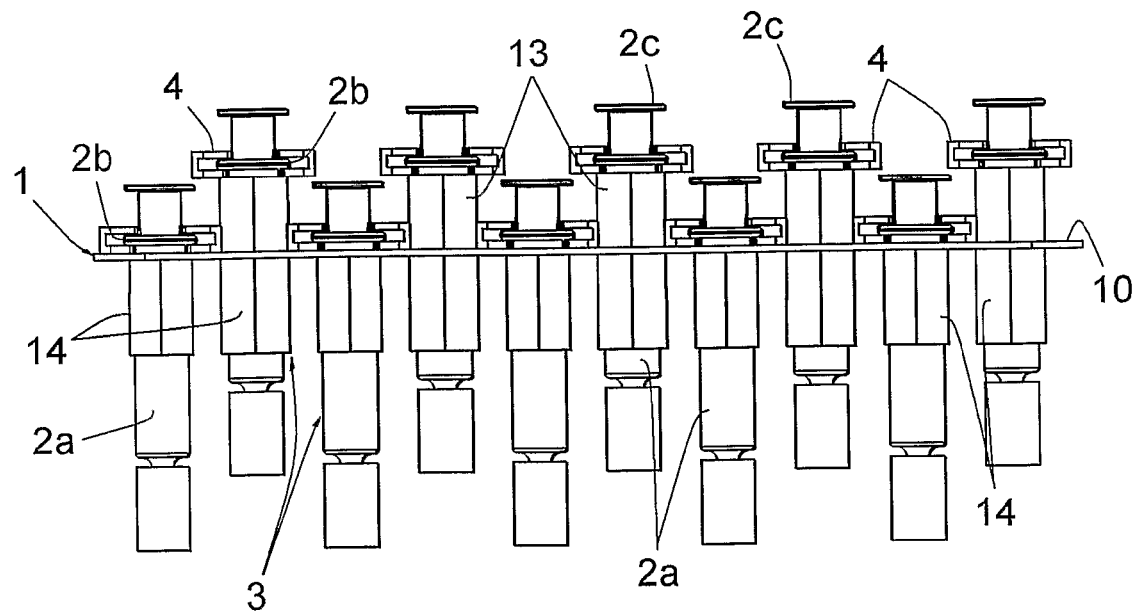
FIG. 10 is a side view of the tray of FIG. 9.
Figure 11:
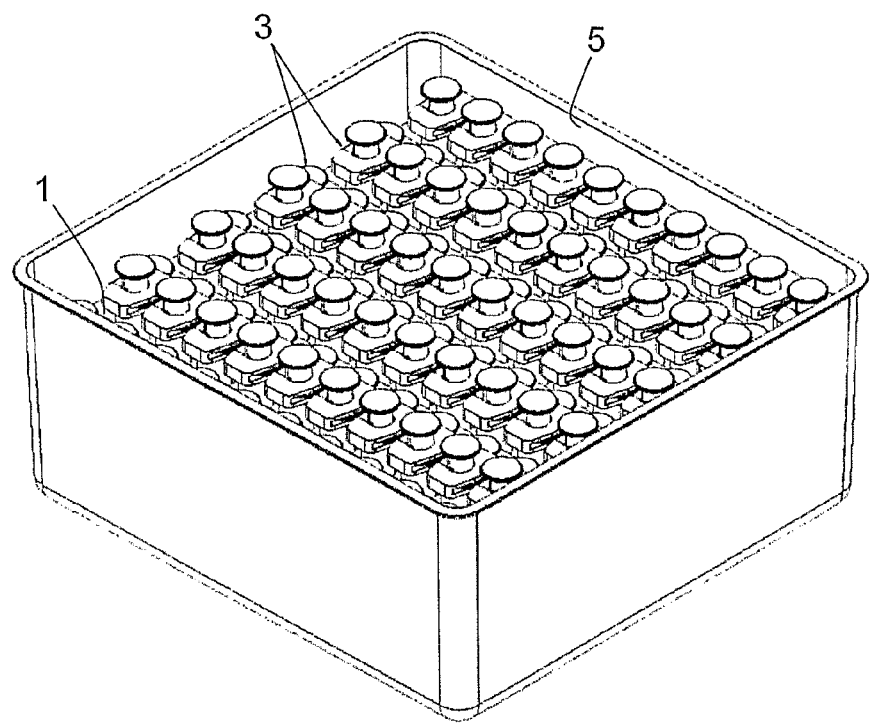
FIG. 11 is a perspective view of the tray of FIG. 9 after a putting in place within a packaging box.
Figure 12:
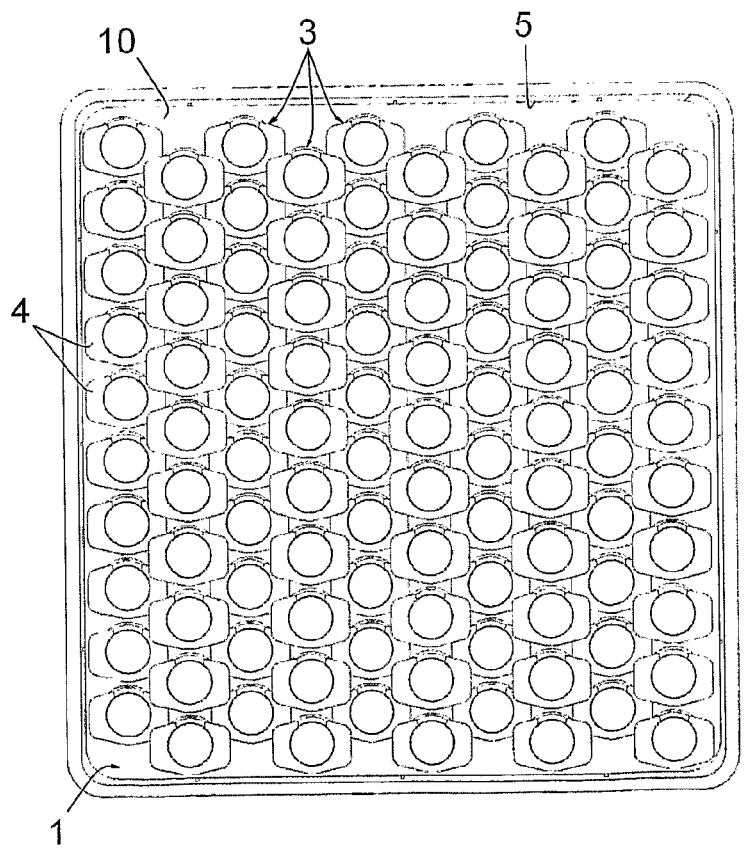
FIG. 12 is a top plan view of the tray of FIG. 9 within the packaging box.

The syringe bodies 2 or syringes 3 can be introduced in these conduits as from the openings 12a and 12b until the flanges 2b or 4 bear against the plate 10 concerning the bodies 2 or syringes 3 introduced in the openings 12a and against the free edges 13a of the chimneys 13 concerning the bodies 2 or syringes 3 introduced in the openings 12b (FIGS. 4 and 9).

Figure 5:
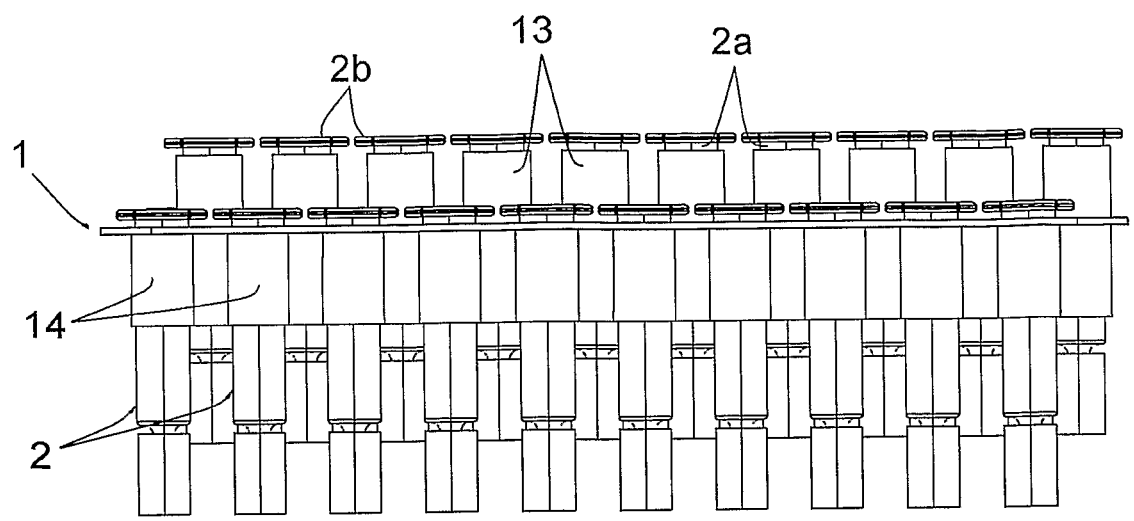
FIG. 5 is a side view of the tray of FIG. 4.
Figure 6:
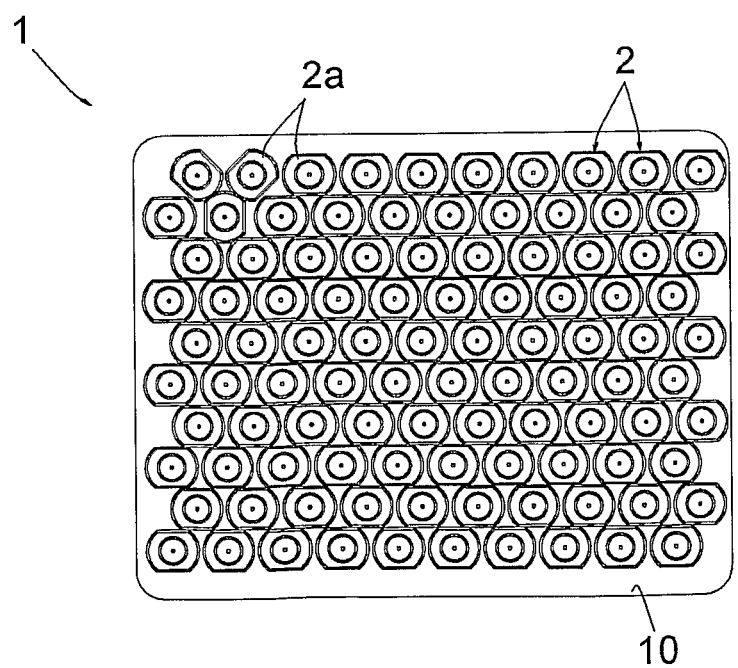
FIG. 6 is a top plan view of the tray.

It can be seen on FIGS. 4-6, particularly on FIG. 6, that the respective distances between the openings 12a and 12b and the height of the chimneys 13 are such that the flanges 2a of the syringe bodies 2 engaged in the openings 12b can rotate in these opening and can overlap without contact with the flanges 2a of the syringe bodies 2 engaged in the openings 12a.

The respective bearing surfaces formed by the plate 10 around the opening 12a and by the free edges 13a of chimneys 13 around the opening 12b thus make it possible to position the flanges 4 at different heights from one row 11a or 11b to an adjacent row 11b or 11a, so that the flanges 2a can rotate and overlap without contact.

It is thus possible to arrange the openings 12a, 12b in positions notably closer than the openings of a tray according to the prior art, and thus to significantly increase the density of the syringe bodies 2 or syringes 3 on a tray 1, while allowing the external dimensions of this tray 1 to remain identical to those of the existing trays. This conservation of these external dimensions is indeed necessary not to induce too important modifications of the automated treatment units of the syringe bodies 2, in particular of the units for handling and/or filling these syringe bodies.

Figure 7:
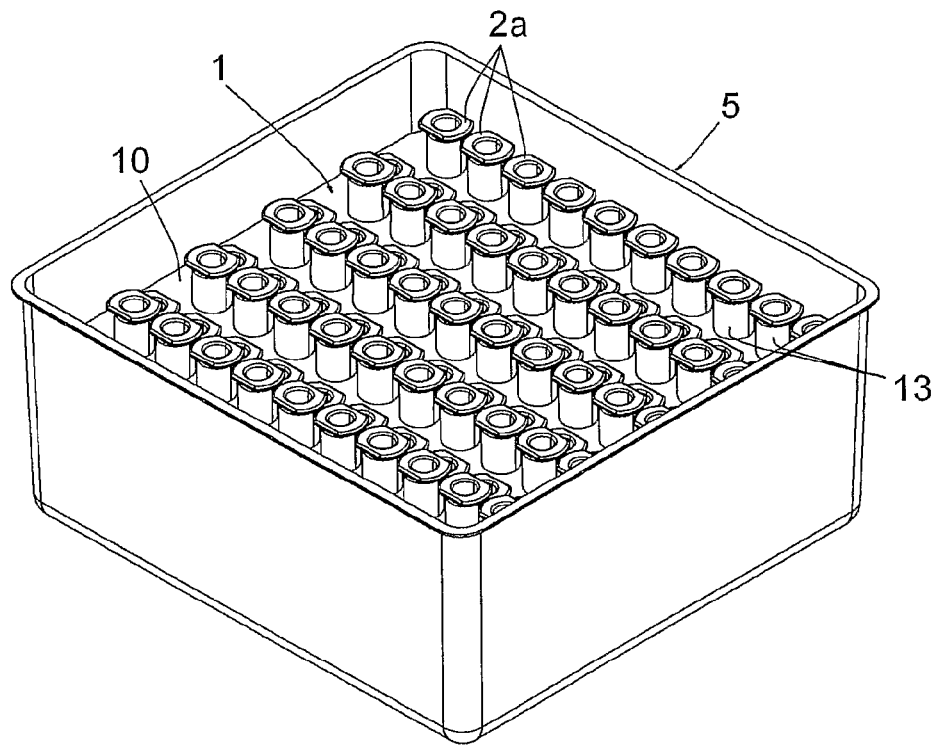
FIG. 7 is a perspective view of the tray of FIG. 4 after a putting in place within a packaging box.

This increase in the density of the number of syringe bodies 2 makes it possible to reduce the number of packagings that are necessary for the conditioning and the transport of a given number of syringe bodies, and thus to reduce the costs of conditioning and transporting these syringe bodies. The subsequent operations of opening and handling the boxes 5 of FIG. 7 are also reduced accordingly.

Figure 8:
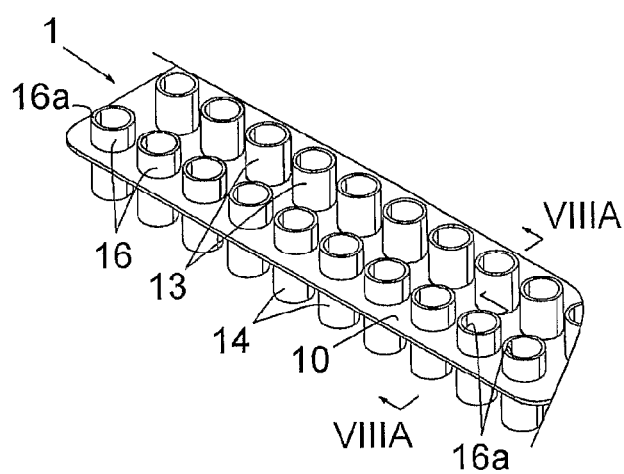
FIG. 8 is a partial perspective view of the tray according to a second embodiment.
Figure 8A:
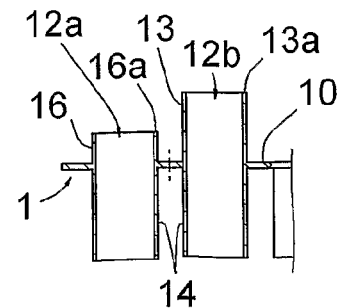
FIG. 8A is a partial side view of the tray of FIG. 8, in cross section along the line VIIIA-VIIIA of FIG. 8.

FIGS. 8 and 8A show an embodiment of the tray 1 in which this tray has chimneys 16 which free edges 16a form the openings 12a, these chimneys 16 having a height smaller than that of the chimneys 13. The syringe bodies 2 are positioned on this tray 1 like indicated above in reference to FIG. 1-7, but with the flanges 2b bearing on the free edges 16a of the chimneys 16.

FIGS. 9-12 show the tray 1 with syringes 3 in lieu of just syringe bodies 2. II can be seen particularly on FIG. 12 that the flanges 4 of the syringes 3 engaged in the openings 12b are able to partially overlap the flanges 4 of the syringes 3 engaged in the openings 12a, without contact with these flanges 4. The density of syringes 3 on the tray 1 can thus be further increased accordingly.

Figure 13:
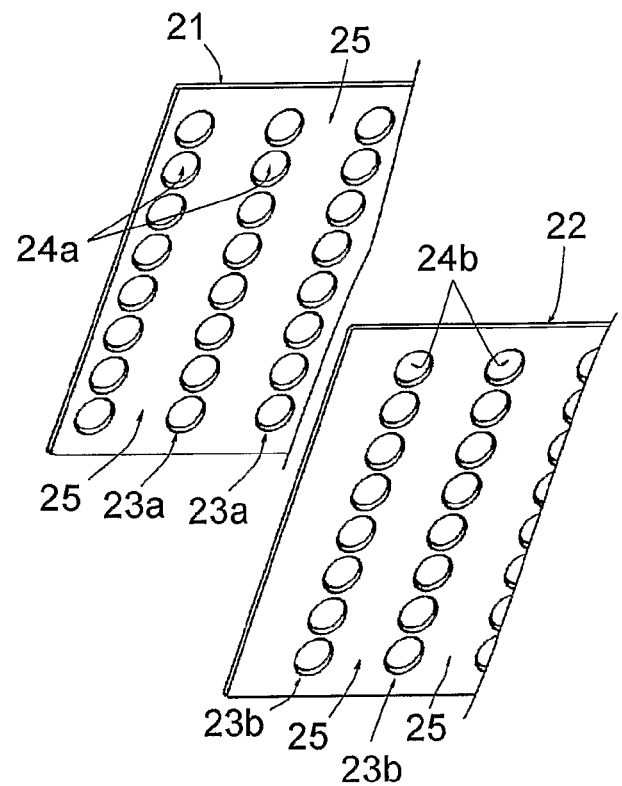
FIG. 13 is a partial perspective view of two other trays.
Figure 15:
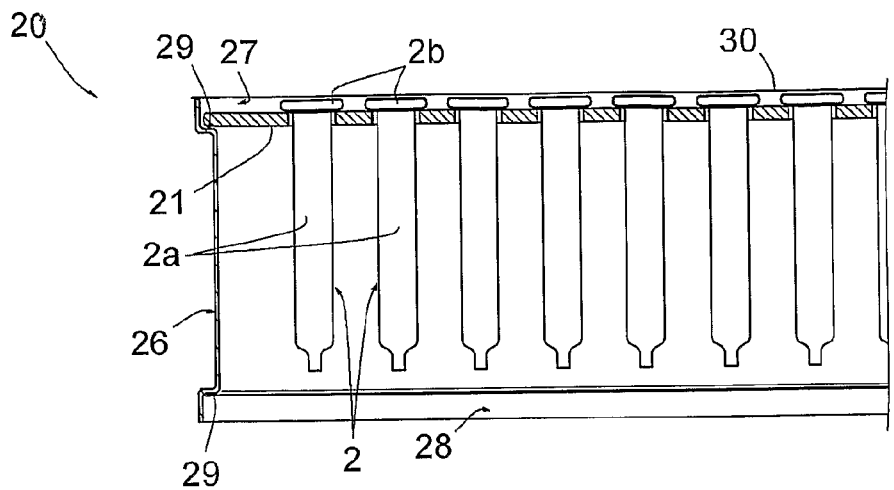
FIG. 15 is a cross-sectional view of a packaging box in which is placed one of the trays of FIG. 13 having syringe bodies thereon.
Figure 16:
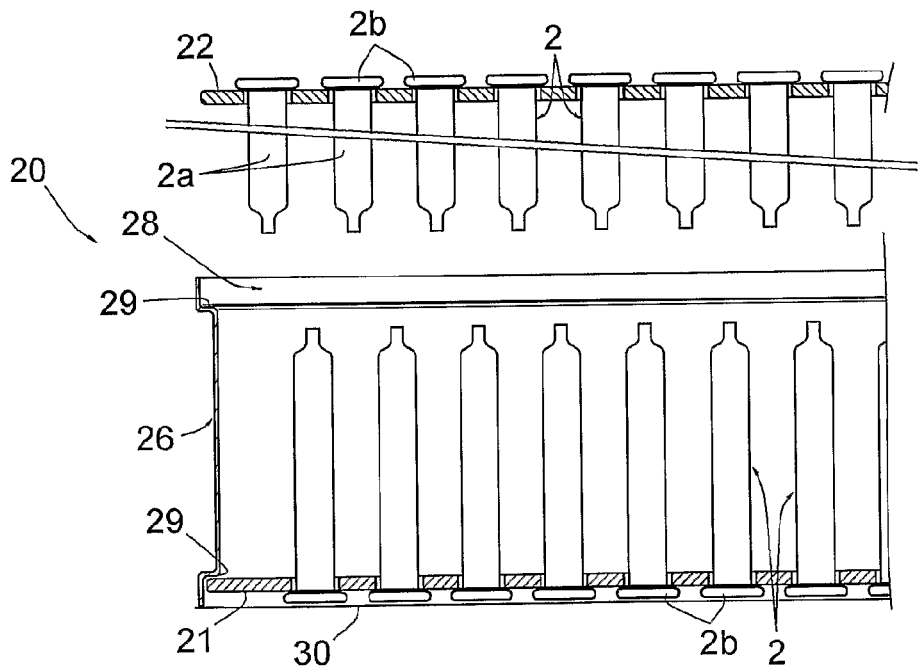
FIG. 16 is a view of the packaging box being turned upside down, before putting in place the second tray of FIG. 13 having syringe bodies thereon.
Figure 17:
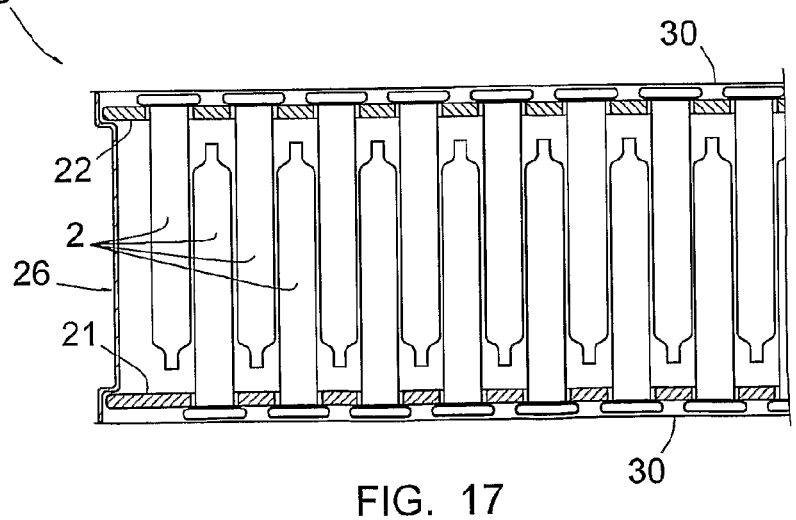
FIG. 17 is a view of the packaging box of FIG. 16 after putting in place said second tray and sealing the box.

FIG. 13 shows two trays 21, 22 of a packaging unit 20 shown on FIGS. 15-17 in which the syringe bodies 2 imbricate.

Figure 14:
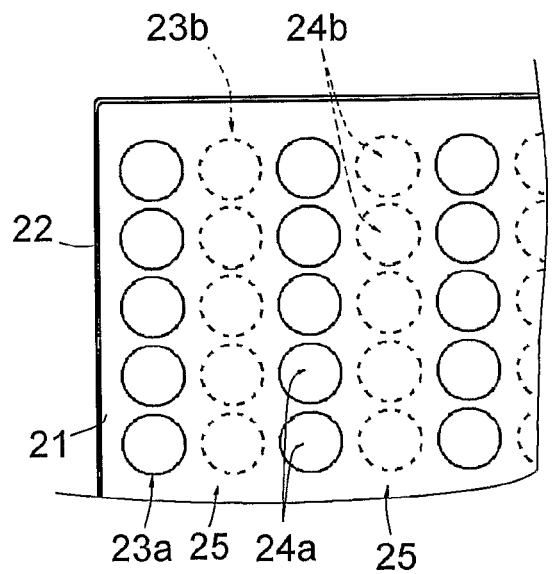
FIG. 14 is a top plan view of the trays of FIG. 13 when these trays are superimposed.

The trays 21, 22 includes rows 23a, 23b of openings 24a and 24b for receiving the syringe bodies, these rows being separated by intermediate portions 25 of the plates of the trays 21, 22 deprived of openings. The rows 23a of one tray 21 are offset with respect to the rows 23b of the other tray 22 such that the openings 24a of one tray 21 are opposite said intermediate portions 25 of the other tray 22 when the edges of the trays 21, 22 are superimposed one another as shown on FIG. 14, and vice versa.

In reference to FIG. 15, the packaging unit 20 includes a box 26 with two opposite openings 27, 28 and with circumferential shoulders 29 for receiving the respective trays 21, 22 thereon. Each shoulder 29 is arranged at a distance of the free edges of the box 26 forming the corresponding opening 27, 28 such that, when a membrane 30 is sealed on these free edges, this membrane 30 will extend along the flanges 2b or 4 of the syringe bodies 2 or syringes 3, thus preventing substantial movement of these syringe bodies 2 or syringes 3 through the openings of the trays 21, 22.

In use, one of the trays 21 with syringe bodies 2 thereon is introduced in the upper opening 27 until its edges bear on the corresponding shoulder 29, and a membrane 30 is then sealed on the free edges of the box 26 forming this opening 27 (FIG. 15). The box 26 is then turned upside down to put the opening 28 upwards (FIG. 16) and the other tray 22 with syringe bodies 2 thereon is introduced in the opening 28 thus placed in the upper position until its edges bear on the corresponding shoulder 29. During this introduction, the syringe bodies 2 of this other tray 22 imbricate with the syringe bodies 2 of the first tray 21. A membrane 30 is then sealed on the free edges of the box 26 forming this opening 28 (FIG. 17).

In a general manner, the packaging unit 20 is used for positioning any kind of elongated objects and includes a support structure (formed in the embodiment of FIGS. 15-17 by the box 26) for supporting the first tray 21, this support structure including a first reception area (the shoulder 29) for receiving said first tray 21; this first tray 21 includes openings 24a for the reception of the elongated objects 2 or 3. The packaging unit 20 further includes a second tray 22 with openings 24b for the reception of elongated objects 2 or 3 and said support structure 26 includes a second reception area (the shoulder 29), intended to receive this second tray 22, this second reception area 29 being arranged so as to position this second tray 22 on said support structure 26 opposite the first tray 21 and so that the openings 24b of said second tray 22 are offset with respect to the openings 24a of said first tray 21. This offset is such that each opening 24a of the first tray 21 is located apart from the perimeter of each opening 24b of the second tray 22, this second tray 22 being positioned with respect to the first tray 21 such that elongated objects 2 or 3 engaged in the openings 24a of the first tray 21 can imbricate with elongated objects 2 or 3 engaged in the openings 24b of the second tray 22, and vice versa.

According to another feature, said support structure is constituted by the packaging box 26, said first and second reception areas being formed by respective bearing surfaces 29 arranged on the walls of this box 26.

According to another feature, said first tray 21 and said second tray 22 are identical one to the other, and said first reception area 29 and second reception area 29 are formed so as to position the edges of the two trays in an offset way one with respect to the other, thus allowing the above-mentioned offset of the openings 24a, 24b of the trays 21, 22.

As appears from the preceding, the invention provides a tray for positioning elongated objects, in particular syringe bodies, allowing to substantially increase the density of the number of elongated objects that can be placed on a same tray, which makes it possible to reduce the number of packagings that are necessary for the conditioning and the transport of a given number of these objects, and thus to reduce the costs of conditioning and transporting these objects. The subsequent handling operations of these objects are thus reduced accordingly.

The invention was described above in reference to embodiments provided purely as examples. It goes without saying that it is not limited to these embodiments, but that it extends to all embodiments covered by the appended claims.

The invention claimed is:

1. A tray for positioning elongated objects, each comprising a body and a flange, the tray including a plate with spaced apart openings intended to receive the bodies of the elongated objects and bearing surfaces near said openings to receive the flanges of the elongated objects when the bodies of the elongated objects are engaged in said openings;

wherein the tray includes at least one first bearing surface near a first opening, located at a first distance from the plate of the tray, and at least one second bearing surface near a second opening adjacent said first opening, located at a second distance from the plate of the tray, said second distance being different from said first distance; and a difference between said first and second distances is such that the flange of an elongated object engaged in one of these openings is able to rotate in this opening without contact with the flange of an elongated object when engaged in the other of these openings.

2. A tray according to claim 1, wherein said first and second openings are located at a distance one with respect to the other such that the flange of the object engaged in one of these openings is able to partially overlap the flange of the object engaged in the other of these openings, and a difference between said first and second distances is such that the flange of a first elongated object engaged in one of these openings is able to partially overlap the flange of a second elongated object engaged in the other of these openings without contact between the flange of the first elongated object and the flange of the second elongated object.

3. A tray according to claim 1, wherein said at least one first bearing surface coincides with the surface of the plate of the tray, being thus formed by this surface.

4. A tray according to claim 1, wherein said at least one first bearing surface does not coincide with the surface of the plate of the tray, being thus formed by a projection which the plate of the tray includes.

5. A tray according to claim 4, wherein said projection is in the form of one or several walls or studs.

6. A tray according to claim 4, wherein said projection is in the form of a chimney coaxial to said first opening.

7. A tray according to claim 4, wherein said projection is in the form of a tubular wall coaxial to said first opening.

8. A tray according to claim 1, wherein the openings of the tray are arranged according to series of openings, each opening of a first series having said first bearing surface and each opening of a second series of openings, adjacent to said first series, having said second bearing surface.

9. A tray according to claim 8, wherein the plate includes alternated first and second series of openings, the bearing surfaces of the first series of openings being formed by the surface of the plate of the tray and the bearing surfaces of the second series of openings being formed by the free edges of chimneys, each chimney being coaxial to one opening of the second series.

10. A tray according to claim 8, wherein the plate includes first, second, . . . , n−1, n series of openings and first, second, . . . , n−1, n series of bearing surfaces respectively associated with each one of these series of openings, the first bearing surfaces of the first series of openings being located at a first distance from the plate of the tray, the second bearing surfaces of the second series of openings being located at a second distance from the plate of the tray higher than said first distance, and the n bearing surfaces of the n series of openings being located at a distance from the plate of the tray higher than a distance that the n−1 bearing surfaces of the n−1 series of openings are located from the plate of the tray.

11. A tray according to claim 8, wherein the plate includes alternated first and second series of openings, the bearing surfaces of the first series of openings being formed by the surface of the plate of the tray and the bearing surfaces of the second series of openings being formed by the free edges of tubular walls, each tubular wall being coaxial to one opening of the second series.

12. A tray according to claim 1, wherein the elongated bodies are one of syringe bodies or syringes.

* * * * *